United States Patent [19]

Harris et al.

[11] Patent Number: 4,871,683

[45] Date of Patent: Oct. 3, 1989

[54] APPARATUS AND METHOD USING A NEW REACTION CAPSULE

[75] Inventors: Paul C. Harris, Edmonds, Wash.; Linda J. Stone, Chino, Calif.

[73] Assignee: Beckman Instruments, Inc., Fullerton, Calif.

[21] Appl. No.: 2,908

[22] Filed: Jan. 13, 1987

Related U.S. Application Data

[63] Continuation-in-part of Ser. No. 724,711, Apr. 18, 1985, abandoned.

[51] Int. Cl.[4] .................... G01N 33/53; G01N 33/545; G01N 35/02

[52] U.S. Cl. .................................... 436/531; 422/64; 435/7; 436/807; 436/808

[58] Field of Search ............... 436/807, 808, 810, 531; 435/7; 422/64

[56] References Cited

U.S. PATENT DOCUMENTS

| | | | |
|---|---|---|---|
| 1,020,344 | 3/1912 | Clauson . | |
| 1,968,711 | 7/1934 | Savy | 259/1 |
| 3,310,292 | 3/1967 | Moore | 259/72 |
| 3,404,780 | 10/1968 | Jungner | 210/142 |
| 3,775,170 | 11/1973 | Rosenblatt | 117/138.8 |
| 3,825,410 | 7/1974 | Bagshawe | 23/230 |
| 3,865,548 | 2/1975 | Padawer | 23/230 |
| 3,918,909 | 11/1975 | Arlman | 23/253 |
| 4,090,850 | 5/1978 | Chen et al. | 23/259 |
| 4,092,408 | 5/1978 | Litt | 424/1 |
| 4,104,026 | 8/1978 | Brooker | 436/808 X |
| 4,138,474 | 2/1979 | Updike | 436/810 X |
| 4,194,041 | 3/1980 | Gore et al. | 428/315 |
| 4,244,694 | 1/1981 | Farina et al. | 23/230 |
| 4,248,965 | 2/1981 | Mochida et al. | 435/7 |
| 4,271,123 | 6/1981 | Curry | 436/808 X |
| 4,457,893 | 7/1984 | Takekawa | 422/64 |
| 4,458,020 | 7/1984 | Bohn | 436/810 X |
| 4,632,901 | 12/1986 | Valkirs | 436/807 X |

FOREIGN PATENT DOCUMENTS

| | | | |
|---|---|---|---|
| WO82/03690 | 10/1982 | PCT Int'l Appl. | 33/50 |
| WO83/01119 | 3/1983 | PCT Int'l Appl. | 35/2 |
| 2139519A | 11/1984 | United Kingdom | 29/36 |

OTHER PUBLICATIONS

Chemplast Zitex Catalog No. C100, Chemplast, Inc., Wayne, N. J.

Sturgeon and Rubio Abstract No. 498 in *Clinical Chemistry*, vol. 30, No. 6.

*Primary Examiner*—Christine M. Nucker

*Attorney, Agent, or Firm*—William H. May; Arnold Grant; Gary T. Hampson

[57] ABSTRACT

A system and method for performing a clinical assay, both including the use of a reaction capsule having a hydrophobic membrane which may be repeatedly wetted and rendered hydrophobic. A pressure differential across the membrane causes liquid flow therethrough to be initiated and the hydrophobic state is then achieved by flowing gas through the membrane. The system includes a turntable supporting a plurality of reaction capsules and eccentric means for agitating the turntable and capsules. The turntable is rotated to position the capsules at various processing stations, including sample introduction, reagent introduction, wash, substrate introduction and read stations. A single cylinder two-inlet valve may be used, one inlet connected to liquid and a second inlet connected to a gas source, to provide both liquid and gas flow through the membrane.

20 Claims, 4 Drawing Sheets

APPARATUS AND METHOD USING A NEW REACTION CAPSULE

CROSS-REFERENCE TO RELATED APPLICATION

This application is a continuation-in-part of application Ser. No. 724,711, filed Apr. 18, 1985.

FIELD OF THE INVENTION

The present invention relates to the field of reaction capsules for performing clinical assays. More particularly, the present invention relates to apparatus and methods for performing clinical assays and a new reaction capsule for use therewith. Examples of clinical assays suitable for use with the new reaction vessel include immunoassays, infectious disease testing, therapeutic drug monitoring and hybridization probe assays such as for genetic disease testing and detection of cancer.

BACKGROUND

Many clinical assays require multiple fluid transfers and manipulations such as addition of reactants, mixing, separation of solid and liquid phases, removal of unreacted components and undesired reaction products, and washing, etc. Oftentimes these steps have to be repeated over and over to produce the desired end result. The manipulations involved are time consuming and difficult to automate. This is a distinct disadvantage in the clinical laboratory where both time and resources are at a premium.

This problem is best exemplified in the case of immunoassays, which are techniques for determination of the presence or concentration of antigenic substances, such as those associated with a wide variety of physiological disorders, in serum or other bodily fluids. These techniques are based upon formation of a complex between the antigenic substance being assayed and an antibody or antibodies in which one or the other member of the complex may be labeled. The label, such as an enzyme or a radioactive element like $I^{125}$, permits detection and/or quantitative analysis after separation of the complexed labeled antigen or antibody from uncomplexed lambed antigen or antibody.

In a sandwich immunoassay, which is one type of immunoassay technique, an antibody bound to a solid support, such as the side wall of a reaction capsule, is contacted with the fluid sample being tested. The antibody is complementary to, i.e., will complex with, a particular sought-for antigen. If present in the sample the sought-for antigen will bind to the antibody and thus the solid support. After a suitable incubation period the solid support is washed to remove the residue of the fluid sample and unreacted antigen, if any. The antibody-antigen complex on the support is next contacted with a solution containing a known quantity of labeled antibody. The labeled antibody will also complex with the sought-for antigen. After a second incubation period to promote complexing the support is again washed to remove any unreacted labeled antibody.

In a simple "yes/no" sandwich immunoassay to determine whether or not the sought-for antigen is present in the fluid sample the washed solid support is tested to detect the presence of the labeled antibody. If the label is a radioactive element, such as $I^{125}$, this can be accomplished by measuring emitted radiation. The amount of labeled antibody detected is compared to that for a negative control sample known to be free of the antigen. Detection of labeled antibody in amounts significantly above the background levels demonstrated by the negative control is interpreted as indicating the presence of the sought-for antigen. Quantitative determination can be made by comparing the measure of labeled antibody with that obtained for standard samples containing known quantities of the sought-for antigen.

If the label is an enzyme, a compatible substrate, i.e., one which will be catabolized by the enzyme, is added to the reaction vessel. The action of the enzyme on the substrate may produce a change in color which would be indicative of the presence of the sought-for antigen. If quantitation is desired a substrate can be selected which, when catabolized by the enzyme, produces a measurable substance such as a fluorescing molecule. After the reaction with the enzyme has been completed the substrate is removed and the amount of fluorescing molecule generated is determined using, for example, fluorescence photometry. The concentration of the sought-for analyte may then be determined using a calibration relationship which relates the quantity of measurable substance to the quantity of the sought-for antigen in the fluid sample.

The same or similar problems of multiple fluid transfers and manipulations and repetition of steps are associated with other types of clinical assays such as infectious disease testing, therapeutic drug monitoring and hybridization probe assays.

One attempt at solving this problem with immunoassays has been to configure the solid support as a filter at the bottom of the reaction capsule. Thus, if present, the sought-for analyte will be complexed with the labeled antibody and bound to the filter. The measurable substance resulting from the action of the enzyme label on the substrate precipitates directly onto the filter leaving, for example, a colored dot on the filter. Such a colored dot is, however, difficult to quantitate with any degree of accuracy and thus such a test is, at best, a qualitative determination.

The use of a filter as a part of a reaction capsule is also known in other forms of immunoassays and, in particular, in radioimmunoassays where the filter may be of a hydrophobic material. Once the reaction within such a radioimmunoassay reaction vessel has taken place, pressure is applied to the fluid within the capsule, causing the filter to become wetted and allowing the fluid to be drawn from the reaction capsule through the filter. Once the filter is wetted, it is then not possible to terminate fluid flow through the filter. Such a characteristic of the filter material is not a disadvantage with radioimmunoassays in that such assays require fluid to be drawn from a reaction capsule through the filter only once. Were such a filter to be used in enzyme immunoassays, however, it would also be necessary to include external valves to stop fluid flow through the filter once it had been wetted. Such external valves add considerable cost and complexity to an immunoassay apparatus, particularly if the apparatus is automated and individual reaction capsules are to be discarded after a single use.

SUMMARY

The present invention is directed to an apparatus and method which overcome the limitations and disadvantages of the prior art. The system and method greatly simplify the manipulations required of the reaction capsule and are particularly suited to an automated instrument.

The system and method of the present invention both include the use of a reaction capsule employing a filter of a hydrophobic material having heretofore unrecognized and unused properties. Fluid flow through the filter may be initiated by the reaction of a pressure differential across the filter. Advantageously, fluid flow may be terminated with the filter returning to a hydrophobic state by flowing a gas through the filter. The novel application of the filter in accordance with the present invention creates an inexpensive and reliable valve that may be formed integrally with the reaction capsule and further enabling the performance of clinical assays without the cumbersome fluid handling devices and techniques known in the prior art. The inexpensive nature of the reaction capsule allows a user of the system and method to discard the capsule after use, further simplifying and reducing the cost of clinical assays and substantially reducing the likelihood of carryover contamination between serial assays performed in a single reaction capsule as was common in the prior art.

The system may further include a wheel or carousel for supporting a plurality of the reaction capsules, the wheel supported at the center by means of an offset cam rotatable by a motor. Actuation of the motor creates a vortex action within the reaction capsules carried by the wheel to thoroughly agitate the fluids contained within the reaction capsules. A novel single-chamber two-inlet pump may be employed in the system to force fluid and then gas through the filter in a reaction.capsule, thus combining both liquid and gas pumping within a single assembly.

DETAILED DESCRIPTION OF THE INVENTION

Figure 1:
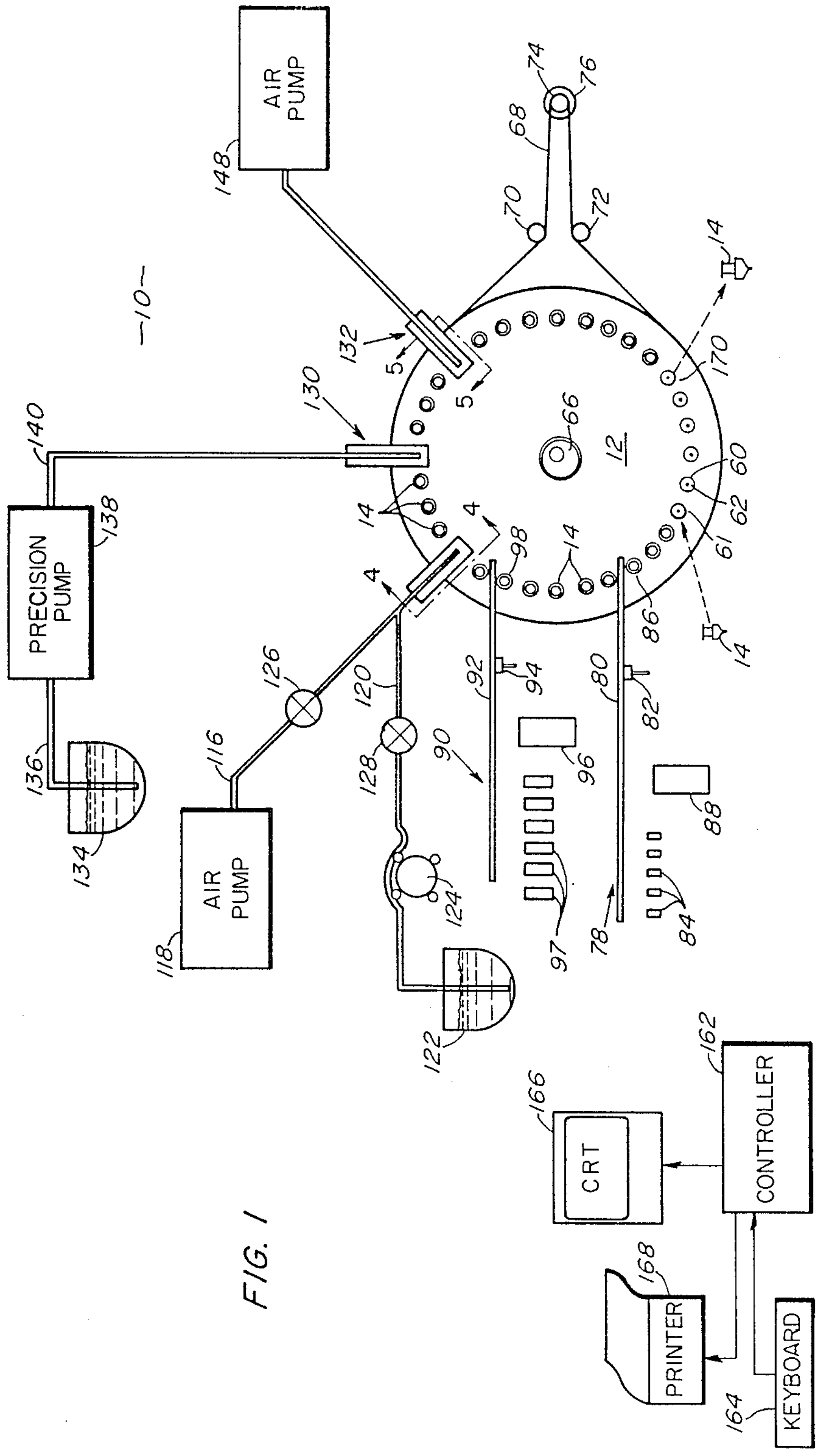
FIG. 1 is a simplified schematic diagram of an immunoassay apparatus in accordance with the present invention.
Figure 2:
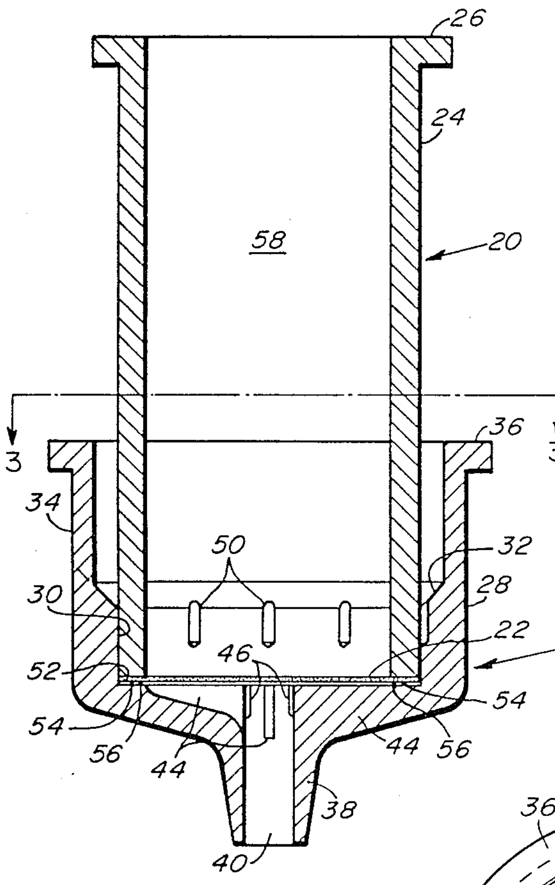
FIG. 2 is a reaction capsule in accordance with the present invention useful with the system of FIG. 1 and shown in section along a central axis thereof.
Figure 3:
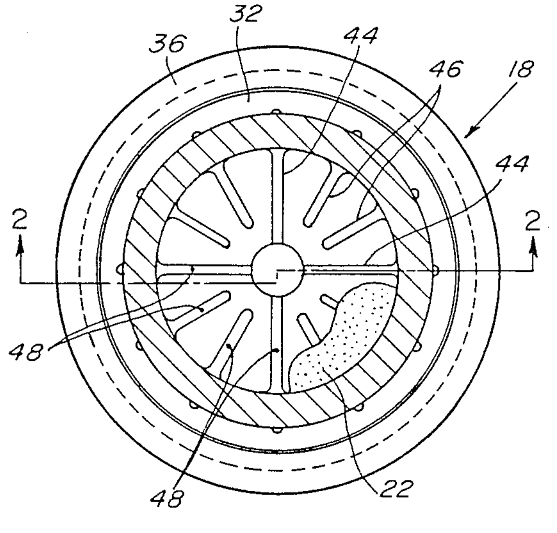
FIG. 3 is a sectioned view of the reaction capsule of the present invention taken along line 3—3 of FIG. 2.

With reference to FIGS. 1-3, a system 10 in accordance with the present invention includes a horizontal turntable 12 which supports a plurality of reaction capsules shown generally at 14. Each capsule 14 comprises a lower section 18, an upper section 20, and a filter 22. The upper section 20 comprises a cylindrical tubular section 24 open at both ends with an outwardly projecting annular flange 26 at the upper end thereof.

The lower section 18 includes a cylindrical base portion 28 having an inside surface 30 adapted to snugly receive the outside surface at the lower end of the tubular section 24. The inside surface 30 joins a tapered surface 32 which tapers outwardly to join the base portion 28 to a cylindrical wall section 34. The upper end of the cylindrical wall section 34 is formed as an outwardly projecting annular flange 36.

The base portion 28 tapers downwardly into a funnel tension 38 forming an interior passage 40 which is open at 44 which similarly extend from the wall of the base portion 28 toward the passage 40. The supports 44 and struts 46 each have coplanar support surfaces 48 adapted to support the filter 22. The inside surface 30 includes a plurality of semicircular grooves 50 extending from the tapered surface 32 to approximately half the distance between the surface 32 and the support surfaces 48.

The filter 22 is sandwiched between an annular surface 52 within the base portion 28 and the bottom annular edge of the cylindrical tubular section 24. The annular surface 52 may include two raised rings 54 and 56 which serve to grip the filter 22. The upper portion 20 is cemented within the lower portion 18 to secure the filter 22 within the capsule 14.

In accordance with the present invention, the filter 22 is selected of a hydrophobic material that enables the capsule 14 to retain fluid within a reaction chamber 58 defined by the upper section 20 and the filter 22. In the embodiment disclosed herein, the volume of the reaction chamber 58 is about one milliliter. The reaction chamber 58 may also hold a solid support useful in a clinical assay such as an immunoassay. With the filter 22 in its hydrophobic state, aqueous liquid at atmospheric pressure within the capsule does not wet the filter 22 and the filter 22 thus retains such liquid within the capsule 14. Advantageously, upon the application of pressure to the reaction chamber 58, the liquid wets the filter 22, allowing liquid to flow therethrough, through the passage 40 and out of the funnel extension 38. To terminate fluid flow, gas may be flowed through the reaction chamber 58, filter 22 and the passage 40 to remove wetting liquid from the pores of the filter and to thus return the filter to a non-flowing or hydrophobic state. Once returned to the hydrophobic state, the filter 22 will again hold liquid at atmospheric pressure within the capsule 14.

Thus, the filter 22 effectively forms a simple, inexpensive liquid valve with no moving parts, an important advance particularly with respect to clinical assays as discussed above. In the embodiment disclosed herein for aqueous reagents and wash solutions, the filter 22 is made from a sintered tetrafluoroethylene matrix membrane material approximately 0.005 inch thick, having a functional pore size of from about 0.2 to about 20 microns, preferably from about 1 to about 6 microns and most preferably about 1 to about 2 microns. An example of such a material having pore sizes in the upper end of the foregoing range includes a material available from Chemplast, Inc. of Wayne, N.J. under the trademark "Zytex", catalog number A-145, type E249-122 as set forth in Chemplast publication No. C100-10M680N. Another example of such a material at the lower end of the foregoing range is discussed in this same publication, namely the Zytex G-100 series, and in particular the type G-110 material.

Pore sizes at the lower end of the foregoing range are particularly useful in infectious disease testing involving techniques such as microbial entrapment. Pore sizes at the high end of the range are applicable with clinical assays which use one or more reagents coated onto particles such as activated cellulose. Some clinical assay reagents contain varying amounts of surfactants. When present in only modest amounts the surfactants do not have any deleterious effect on the filters of the present invention. However, higher amounts of surfactants can disrupt the hydrophobic nature of such filters having pore sizes at the higher end of the foregoing range. Pore sizes within the preferred range are not subject to such effect.

With reference again to FIG. 1, the reaction capsules 14 are received by the turntable 12 within suitable restraining means 60 at a loading station 61. The restraining means 60 includes a plurality of openings 62 formed vertically through the turntable 12. Each opening 62 is adapted to receive the lower section 18 of the capsule 14 such that the lower surface of the flange 36 rests against the upper surface of the turntable 12 when a capsule 14 is installed on the turntable 12.

The turntable 12 of the system 10 is supported at its center by an offset or eccentric cam 66 for creating a vortex mixing action within the capsules 14 as described below. A flexible belt 68 extends about the periphery of the turntable 12 and is guided by idler wheels 70 and 72 to a drive pulley 74 which is in turn driven by a stepper motor 76.

The system 10 includes a sample delivery subsystem 78 which includes a track 80 supporting a movable probe 82. The subsystem 78 includes suitable drive means for performing the following movements: moving the probe 82 along the track 80; lowering the probe 82 into a selected one of a plurality of sample cups 84; aspirating a quantity of sample into the probe 82; moving the probe 82 to a sample dispensing station 86 over the turntable 12; lowering the probe 82 into the capsule 14 at the station 86; and dispensing the aspired sample into the capsule 14 at the sample dispensing station 86. The subsystem 78 may also include a wash station 88 which washes the probe 82 after a volume of sample has been delivered at the sample dispensing station 86.

The system 10 similarly includes a reagent delivery subsystem 90 similar to the sample delivery system 78. The reagent delivery subsystem includes a track 92, movable probe 94, wash station 96, all adapted to deliver precise quantities of one or more reagents from a plurality of reagent cups 97 to a capsule 14 disposed at a reagent dispensing station 98.

It will be recognized that the sample and reagent delivery subsystems 78 and 90 may be of conventional design as is well known in the automated clinical instrument art. Equivalent means would be equally suitable, such as replacing the subsystems 78 and 90 with a single X-Y subsystem utilizing a single probe head displaced in an X-Y coordinate system over the sample cups 84, reagent vials 96, and a single dispensing station 86 or 98.

Figure 4:
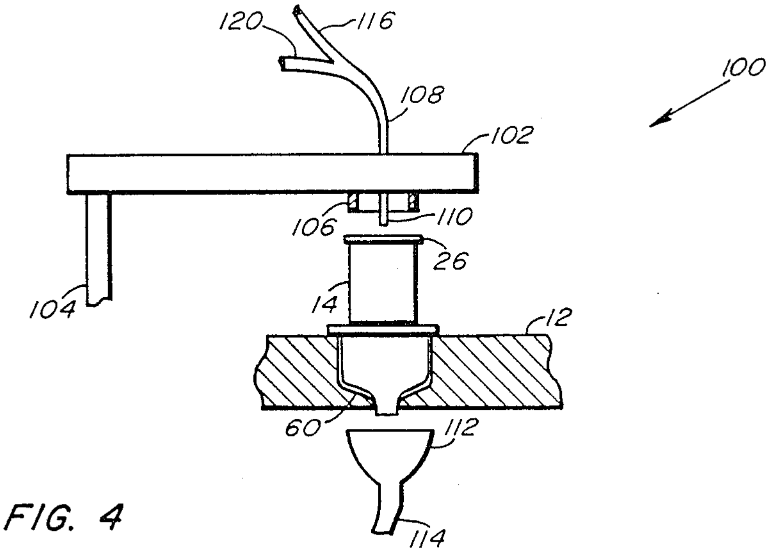
FIG. 4 is a side view of the wash station taken along line 4—4 of FIG. 1.

The system 10 includes a capsule wash station 100. As seen in FIG. 4, the wash station 100 includes a horizontal arm 102 having one end which extends over the turntable 12. A second end of the arm 102 is affixed to an elevator mechanism 104 which is used for raising and lowering the arm 102 with respect to the turntable 12 and the capsules 14 loaded thereon. The elevator mechanism 104 may comprise, for example, a stepper motor driving a lead screw, the lead screw including a threaded member fixed to the arm 102 which, when the stepper motor is rotated, moves the arm 102 up or down.

An annular seal 106 is fixed to the arm 102 above the turntable 12, the annular seal 106 being shown in cross section in FIG. 4. A conduit 108 is fixed to and passes through the arm 102 and is concentrically aligned with the annular seal 106. A lower open end 110 of the conduit 108 extends below the lower surface of the annular seal 106.

A fluid receiving chamber 112 is concentrically aligned with the conduit 108 below the turntable 12. The upper end of the chamber 112 is open and the lower end thereof narrows and is connected to a conduit 114 which conducts waste fluid to a suitable receptacle (not shown).

As seen in FIGS. 1 and 4, the conduit 108 is connected by an air conduit 116 to an air pump 118. The conduit 108 is also connected to a wash solution conduit 120 which is in turn connected to a wash solution reservoir 122 via a peristaltic pump 124. Both the conduits 116 and 120 include solenoid-controlled valves 126 and 128, respectively. The valve 126 controls gas flow from the air pump to the conduit 108 while the valve 128 controls wash solution flow from the pump 124 to the conduit 108.

To perform a wash operation, the turntable 112 may be positioned such that a capsule 14 is coaxially aligned with the conduit 108 and the chamber 112. With the capsule 14 so aligned, the elevator mechanism 104 is operated to lower the arm 102 such that the annular seal 106 is near but not in contact with the annular flange 26 of the capsule 14. Wash solution is then delivered through the conduit 108 to the capsule 14. To remove the wash solution and return the filter to a hydrophobic state as is described more fully below, the elevator mechanism 104 is operated to lower the arm 102 until the annular seal 106 is urged against the flange 26. Air may then be delivered through the conduit 108 into the capsule 14 to blow the wash solution through the filter 22 and out of the capsule 14. Once the wash cycle is completed, the elevator mechanism 104 is actuated to raise the arm 102 and thus the end 110 above the flange 26. The turntable 12 may then be rotated to reposition the capsule 14.

The system 10 further includes a substrate station 130 (FIG. 1) and a read station 132. Liquid substrate from a reservoir 134 is conducted via a tube 136 to a precision pump 138. The precision pump 138 is adapted to pump precise amounts of substrate through a conduit 140 to the substrate station 130. The substrate station 130 is similar to the wash station 100 but is adapted to deliver only liquid substrate to a capsule 14 properly aligned with the substrate station 130.

Figure 5:
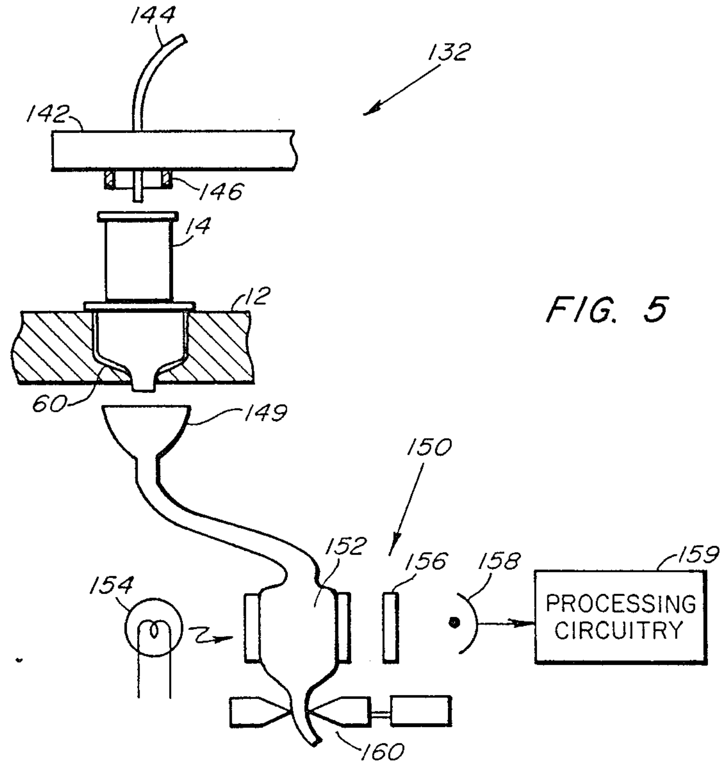
FIG. 5 is a side view of a read station taken along line 5—5 of FIG. 1.

The read station 132 is also similar to the wash station 100 and includes a horizontal arm 142 (FIG. 5) extending over the turntable 12. A single conduit 144 passing through and fixed to the arm 142 is concentrically aligned with an annular seal 146. The conduit 144 leads to an air pump 148. A fluid receiving chamber 149 is disposed beneath the turntable 12 and in alignment with the conduit 144 and annular seal 146. The fluid receiving chamber 149 is in fluid communication with a fluorometer 150 which includes a cell 152 into which substrate from the capsule 14 may flow. A light source 154 directs light at a predetermined wavelength into the cell 152 and fluorescence at a second wavelength passes through a filter 156 and is detected by means of a photodetector 158. The filter 156 and photodetector 158 are disposed at a 90° angle from the cell 152 with respect to the angle of light from the source 154. The output of the photodetector 158 is applied to and processed by circuitry 159 well known in the art to provide an output related to the fluorescence of the substrate. Once the fluorescence measurement has been made, a pinch valve 160 is opened, allowing the substrate to drain from the cell 152 into a suitable waste receptacle (not shown). The system 10 may also include conventional means (not shown) for washing the fluid receiving chamber 149 and the fluorometer 150 after each use. Further, the fluorometer 150 may be replaced by a spectrophotometer adapted to measure absorbance or transmittance of the substrate.

The system 10 is controlled by means of a microprocessor-based controller 162 (FIG. 1) as is well known in the art. The controller is adapted to receive instructions via a keyboard 164 and may output data to a display 166 and a printer 168. The controller 162 controls the operation of the sample delivery subsystem 78, the reagent delivery subsystem 90, the wash, substrate and read subsystems 100, 130 and 132, the peristaltic and precision pumps 124 and 138, air pumps 118 and 148, valves 126 and 128, and stepper motor 76. The controller 162 also responds to the output of the circuitry 159 to analyze the fluorescence measurement and relate such measurement to a standard curve to thereby determine the concentration of an analyte in a sample. All such techniques are well known in the automated clinical analyzer art.

Once all operations with a capsule 14 have been completed, the capsule 14 may be ejected or removed from the turntable 12 at a removal station 170.

The system 10 includes suitable temperature control means as is well known in the art to maintain the turntable 12 as well as the capsules 14 disposed therein at a constant temperature.

A clincial assay such as an immunoassay to be performed on the system 10 begins with the user selecting a capsule 14 which includes an appropriate solid support for the test desired by the user. For example, the selected capsule 14 may include a solid support adapted for a competitive fluorescent enzyme immunoassay for the analyte $T_3$. The capsule 14 may initially have a seal over the flange 26, the seal being removed by the user. The capsule 14 is placed into the restraining means 60 on the turntable 12.

To control the operation of the system 10, the user selects, via the keyboard 164, the particular sample cup 84 from which the sample is to be withdrawn and identifies the test to be performed. Based on the position of the turntable 12, the controller 162 correlates the capsule 14 loaded at the loading station 61 with the selected sample and test and controls the system 10 to perform the specified procedure as will now be described.

The turntable 12 and thus the capsule 14 is rotated by means of the stepper motor 76 and the flexible belt 68 until the capsule 14 is positioned at the wash station 100 where an initial wash or prewash operation is performed. With reference to FIG. 4, the arm 102 is lowered until the annular seal 106 is near but not in contact with the flange 26 of the capsule 14. Approximately 0.5 ml of wash solution from the reservoir 122 is drawn by means of the pump 124 through the opened valve 128, the conduit 120 and the conduit 108 into the capsule 14.

In its initial or hydrophobic state, the hydrophobic nature of the filter 22 causes the filter to repel the aqueous wash solution, thus retaining the wash solution within the reaction chamber 58. In the embodiment disclosed herein, the wash solution may be a saline solution. The arm 102 is then lowered such that the seal 106 contacts and is slightly compressed against the flange 26. The air pump 118 is operated to provide air at approximately 15 psi through the opened valve 156 and conduits 116 and 108 into the capsule 14. The air pressure within the capsule 14 causes the filter 14 to be wetted, allowing the wash solution to be blown through the filter 22 and out of the capsule 14. The wash solution flows into the chamber 112 and through the conduit 114 to the waste container. Once the wash solution has been emptied from the capsule 14, the flow of air through the uniquely selected filter 22 blows liquid from the pores of the filter 22, thus reestablishing the hydrophobic nature of the filter 22.

With the prewash completed, the turntable 12 is rotated so as to place the capsule 14 at the sample dispensing station 86. The sample delivery subsystem 78 is operated to withdraw a predetermined amount of the selected sample from one of the sample cups 84 and deliver the sample volume via the probe 82 into the capsule 14 at the sample dispensing station 86.

The turntable 12 is again rotated to position the capsule 14 at the reagent dispensing station 98. The reagent delivery subsystem 90 is operated to dispense a predetermined volume of one or more selected antibody reagents contained in the reagent vials 97 into the capsule 14. The hydrophobic state of the filter 22 retains the sample and reagent or reagents within the capsule 14. The immunoassay action is then allowed to occur within the capsule 14 and, during such reaction, the contents of the capsule 14 are subjected to the vortex mixing action produced by the eccentric cam 66. The eccentric cam 66 has a throw of approximately 0.1 inch and may be turned at approximately 1250 to 1700 rpm to create the vortexing action within the capsule 14.

Once the immunoassay reaction has been completed, the capsule 14 is moved to the wash station 100 by rotation of the turntable 12. At the wash station 100, sample and reagent or reagents are blown from the capsule 14 and a plurality of wash cycles are performed, each wash cycle including a brief vortex agitation period. When the sample and reagent are blown from the capsule 14 and at the end of each wash cycle, the air flow through the filter 22 reestablishes the hydrophobic state of the filter 22.

The capsule 14 is then moved to the substrate station 130 by rotation of the turntable 12. At the substrate station 130, substrate from the reservoir 134 is added to the capsule 14. The capsule 14 is again agitated using the vortex action and the enzyme reaction is allowed to occur for a predetermined incubation period. At the end of the incubation period, the capsule 14 is moved to the read station 132 and air from the air pump 148 is applied to the capsule 14 to blow the substrate out of the capsule 14 into the cell 152 where the fluorescence of the substrate is measured. In accordance with the fluorescence present in the substrate, the concentration of the analyte in the sample may be determined using well-known techniques.

Although the preceding operational example has been presented for a single capsule 14 performing a single test, the system 10 may perform a number of different clinical assays concurrently for respective capsules 14 which may be loaded onto the turntable 12. In each instance, the controller 162 correlates the location of individual capsules 14 on the turntable 12 with user-specified samples and tests. The specification of the test is used by the controller 162 to select the correct reagent or reagents to be introduced into the respective capsule 14. The controller 162 also provides the necessary timing functions for each capsule 14 according to the specified test. All such control functions are well known and readily apparent to those in the automated clinical analyzer art.

Examples of suitable reagents as well as processing times for various clinical assays are as follows:

Competitive Fluorescent Enzyme Immunoassay

Solid support: Cellulose 50μparticles with goat antirabbit gamma globulin covalently attached.

Prewash: Single wash with 0.5 ml of normal saline, no vortex.

EIA reagents: (1) Specific rabbit antibody; (2) alkaline phosphatase conjugated analyte.

EIA incubation time and vortex: Approximately 10–30 minutes (depending on analyte), with continuous vortex agitation.

Wash, number of cycles: Three wash cycles with 0.5 ml normal saline, vortex agitation of three to five seconds in each cycle.

Substrate: 4-methyl umbilliferone phosphate 0.05 mM.

Substrate Incubation Time and vortex: Approximately 5–30 minutes at 37°±0.2° C., with continuous vortex agitation.

Fluorometry: Source: 360 nm ±2 nm, half bandwidth of 5 nm. Fluorescence: 450 nm ±10 nm, half bandwidth of 10–20 nm.

Sandwich Fluorescent Enzyme Immunoassay

Solid support: Cellulose 50μparticles with 1° antibody covalently attached.

Prewash solution and time: Same as competitive FEIA above.

EIA reagents: Alkaline phosphatase conjugated to 2° antibody.

EIA Incubation time and vortex: Approximately 10–60 minutes (depending on analyte), with continuous vortex agitation.

Wash, number of cycles: Three or four wash cycles (depending on analyte) with 0.5 ml normal saline, vortex agitation of three to five seconds in each cycle.

Substrate: Same as competitive FEIA above.

Substrate Incubation time and vortex: Same as competitive FEIA above.

Fluorometry: Same as competitive FEIA above.

Although the above examples state that vortex agitation is continuous during various incubation times, the vortex agitation during such incubation periods for an assay being conducted in a particular capsule 14 may be interrupted to perform actions required for other capsules 14 on the turntable 12, such as sample, reagent or substrate delivery, wash cycles, and so on.

Microbial Entrapment

Bacterial suspension of $10^4$ to $10^8$ were introduced to a reaction capsule containing a hydrophobic membrane filter. The membrane filter had a functional pore size of about 0.2 microns. A pressure differential was initiated across the filter to first wet the filter and then initiate liquid flow therethrough. Presence of bacteria remaining on the membrane was detected by reduction of iodonitrotetrazolium indicator which turns from colorless to pink on reduction. The reaction capsule was first incubated at 37° C. and was then tested for reduction of dye at 10 minutes, 15 minutes, 2, 4 and 18 hours. Some bacteria could be detected in 10 to 15 minutes. About $10^7$ bacteria per cc can be detected in under 4 hours.

The foregoing example demonstrates the applicability of the reaction capsule of the present invention as a urine screen for bacteria, for the detection of bacteria in spinal fluid and for the screening of blood culture aliquots for bacteria. Other such uses will be readily suggested to those skilled in the art.

Figure 6:
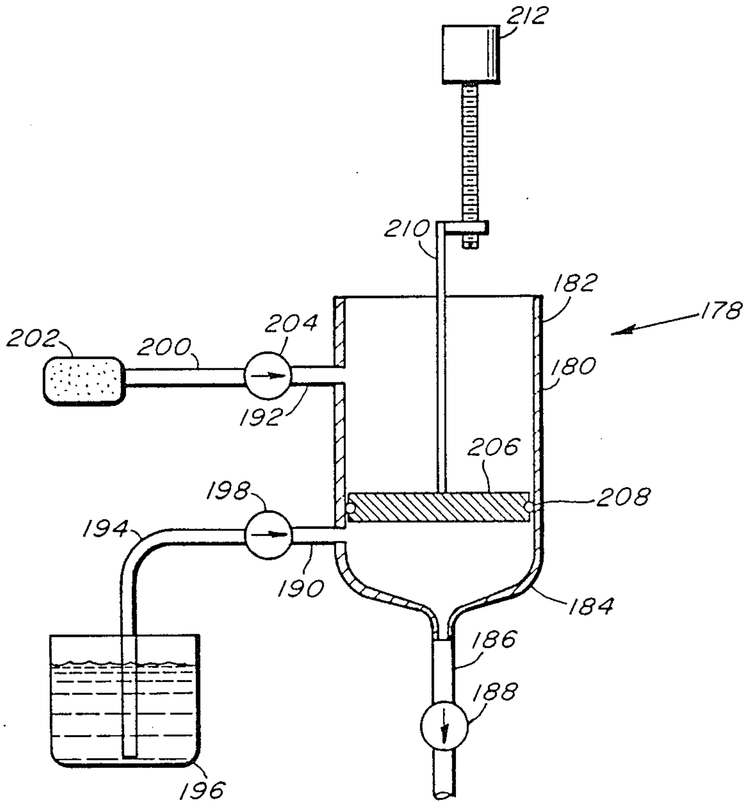
FIG. 6 is a side view shown partially in cutaway and schematic form of a single chamber pump useful with the system of FIG. 1.

The air pump 118 and peristaltic pump 124 of FIG. 1 may be replaced by a unitary pump with few moving parts that provides both the wash solution and the air to blow through the filter 22. Such a pump 178 as shown in FIG. 6 includes a cylindrical chamber 180 having an open upper end 182. The lower end 184 of the chamber 180 is tapered and connected to a conduit 186. The conduit 186 includes a one-way valve 188 and is connected to the conduit 108 (FIG. 4).

The chamber 180 includes two inlets, a first lower inlet 190 and a second upper inlet 192. The lower inlet 190 is connected via conduit 194 to a wash solution reservoir 196. The conduit 194 includes a one-way valve 198 which allows wash solution to flow only from the reservoir 196 to the pump 178.

The upper inlet 192 is connected by a conduit 200 to a suitable source of air at atmospheric pressure which may simply be a filter 202. The conduit 200 also includes a one-way valve 204 which allows air to flow only into the pump 178.

A piston 206 is disposed within the chamber 180, the piston 206 including s suitable seal such as an O-ring 208 between the piston 206 and the inside walls of the chamber 180. The piston 206 is movable up and down within the chamber 180 by means of a rod 210 driven by a stepper motor 212 in turn controlled by the controller 162.

In use, a pump cycle begins with the piston 206 between the inlets 190 and 192 and nearest the inlet 190. The stepper motor 212 is operated to draw the piston 206 upwardly within the chamber 180, drawing wash solution from the reservoir 106 through the conduit 194 and valve 196 into the chamber 180. Wash solution continues to be drawn into the chamber 180 until the piston 206 reaches the upper inlet 192. As the piston 206 moves above the inlet 192, air is drawn through the filter 202, conduit 200 and valve 204 into the chamber 180. Because the air available at the filter 202 is at atmospheric pressure, no further wash solution is drawn from the reservoir 196 as the piston continues to move upwardly within the chamber 180.

To complete the cycle of the pump 178, the stepper motor 212 is operated so as to move the piston 206 downwardly within the chamber 180. The one-way valves 198 and 204 prevent backflow into the conduits 194 and 200. Consequently, wash solution, in the lower portion of the pump chamber 180, is first forced through the conduit 186 and one-way valve 188 into the capsule 14 via the conduit 108 (FIG. 4). Once the wash solution has been emptied from the chamber 180, air within the chamber is then forced through the conduit 186 and valve 188 into the capsule 14. As described previously, the air flowing through the hydrophobic filter 22 places the filter 22 in a hydrophobic state.

Thus, the pump 178 of FIG. 6 provides both wash solution and compressed air to the capsule 14 positioned at the wash station 100, replacing the air pump 118, peristaltic pump 124 and valves 126 and 128, thereby simplifying the system 10 of FIG. 1.

Several alternatives to various aspects of the system 10 may be utilized. For example, an air pump 118 has been disclosed to produce a pressure differential across the filter 22 to first wet the filter 22, thereby initiating liquid flow therethrough, and then blow wetting liquid from the filter 22 pores to return the filter 22 to its hydrophobic state. However, a vacuum may be drawn through the passage 40 to accomplish the same result. Also, although the solid support may be initially contained within the capsule 14 at the time the capsule 14 is placed onto the turntable 12, empty capsules 14 may instead be placed onto the turntable 12. In such an instance, the solid support would be present on the system 10 in the form of a slurry that is pipetted into the capsules 14 via the reagent delivery subsystem 90. The liquid portion of the slurry would first be blown from the capsule by application of air pressure at the wash station, followed by a pre-wash of the solid support as described above.

The foregoing detailed description is not to be construed as limiting the scope of the present invention which is defined in accordance with the appended claims and all equivalents thereof.

What is claimed is:

1. A reaction capsule for performing a clinical assay comprising a tubular member having first and second ends and a membrane closing the first end, the membrane comprising a porous hydrophobic material having a predetermined pore size such that a liquid retained within the tubular member when the membrane is in a hydrophobic state may be expelled through the membrane in response to the application of a pressure differential across the membrane thereby creating liquid flow through the membrane and said liquid flow may be terminated and the membrane returned to the hydrophobic state by flowing gas through the membrane.

2. A capsule as in claim 1 wherein the membrane has a functional pore size of from about 0.2 microns to about 20 microns.

3. A capsule as in claim 1 wherein the membrane has a functional pore size of from about 1 to about 6 microns.

4. A capsule as in claim 1 wherein the membrane has a functional pore size from about 10 to about 20 microns.

5. A capsule as in claim 1 wherein the capsule includes support ribs fixed at the first end and the membrane is supported by the support ribs.

6. A capsule as in claim 5 wherein the capsule further includes solid support means within the tubular member.

7. A clinical assay system comprising:

a reaction capsule comprising a tabular member having first and second ends and a membrane closing the first end, the membrane comprising a porous hydrophobic material having a predetermined pore size such that a liquid retained within the tabular member when the membrane is in a hydrophobic state may be expelled through the membrane in response to the application of a pressure differential across the hydrophobic membrane thereby creating liquid flow through the membrane and said liquid flow may be terminated and the membrane returned to the hydrophobic state by flowing gas through the membrane;

means for introducing liquid into the capsule above the membrane;

means for creating a pressure differential sufficient to cause liquid to flow through the membrane; and means for flowing gas through the membrane to return the membrane to the hydrophobic state.

8. A system as in claim 7 further including a turntable for supporting a plurality of reagent capsules and eccentric means for displacing the turntable to create a vortexing action within the capsules.

9. A system as in claim 7 wherein the introducing means and the flowing gas means comprises a pump having a cylinder, the cylinder including a lower and upper end, the lower end being closed and adapted to be in fluid communication with the capsule, a lower liquid inlet and upper gas inlet, a piston movable within the cylinder, and means for displacing the piston through a stroke which includes the upper inlet.

10. A system as in claim 7 wherein the membrane has a functional pore size of from about 0.2 to about 20 microns.

11. A system as in claim 7 wherein the membrane has a functional pore size of from about 1 to about 6 microns.

12. A system as in claim 7 wherein the membrane has a functional pore size form about 10 to about 20 microns.

13. A method of performing an immunoassay comprising the steps of:

adding a solid support coated with a first analyte, a patient sample containing a second analyte and a third analyte having a label attached thereto to a reaction capsule, the reaction capsule having a hydrophobic membrane at a lower end thereof;

allowing an immunoassay reaction to occur between the first, second and third analytes;

applying pressure to the reaction capsule to initate liquid flow through the membrane; and flowing gas through the membrane to return the membrane to a hydrophobic state.

14. A method as in claim 13 wherein the method further includes the steps of introducing a wash solution into the capsule when the membrane is in a nonfluid-conducting state;

creating a pressure differential across the membrane to initate wash solution flow therethrough; and flowing gas through the membrane to return the membrane to the hydrophobic state.

15. The method as in claim 14 wherein the method further includes;

adding a liquid substrate to the capsule;

allowing a reaction to occur within the capsule between the substrate and the label, the reaction creating a predetermined substance;

creating a pressure differential across the membrane to initate the flow of the liquid and the substance through the membrane;

collecting the substrate and substance in a cell; and measuring the quantity of the substance in the cell to determine an attribute of the patient sample.

16. A method of using a hydrophobic membrane comprising the steps of:

placing the hydrophobic membrane across an open end of a vessel;

introducing liquid into the vessel;

creating a pressure differential across the membrane such that the liquid flows through the membrane; and flowing gas through the membrane to return the membrane to a hydrophobic state.

17. A method as in claim 16 wherein the membrane is made from a material comprising tetrafluoroethylene in a preselected matrix having a pore size in the range of from about 1 to about 6 microns.

18. A method as in claim 16 wherein the membrane is made form a material comprising tetrafluoroethylene in a preselected matrix having a pore in the range of from about 10 to about 20 microns.

19. A method as in claim 16 wherein the membrane is made from a material comprising tetrafluoroethylene in a pre-selected matrix having a pore size in the range of from about 0.2 to about 20 microns.

20. A method as in claim 19 wherein the step of creating the pressure differential includes raising the pressure within the vessel above the pressure outside the vessel.

* * * * *

UNITED STATES PATENT AND TRADEMARK OFFICE
CERTIFICATE OF CORRECTION

PATENT NO. : 4,871,683

DATED : October 3, 1989

INVENTOR(S) : Paul C. Harris, et al.

It is certified that error appears in the above-identified patent and that said Letters Patent is hereby corrected as shown below:

Col. 1, line 45 reads "lambed antigen" should read "labeled antigen".

Col. 4, line 4 reads "tension 38" should read "extension 38".

Col. 11, line 48 (claim 7) reads "a tabular member" should read "a tubular member".

Col. 4, line 5 reads "at 44 which similarly extend..." should read "at the lower end thereof. (new paragraph) The base portion 28 includes a plurality of supports 44 extending from the inner wall of the base portion 28 to the passage 40 and a plurality of struts 46 between the supports 44 which similarly extend..."

Signed and Sealed this

Thirtieth Day of June, 1992

*Attest:*

DOUGLAS B. COMER

*Attesting Officer*

*Acting Commissioner of Patents and Trademarks*